Figure 1:
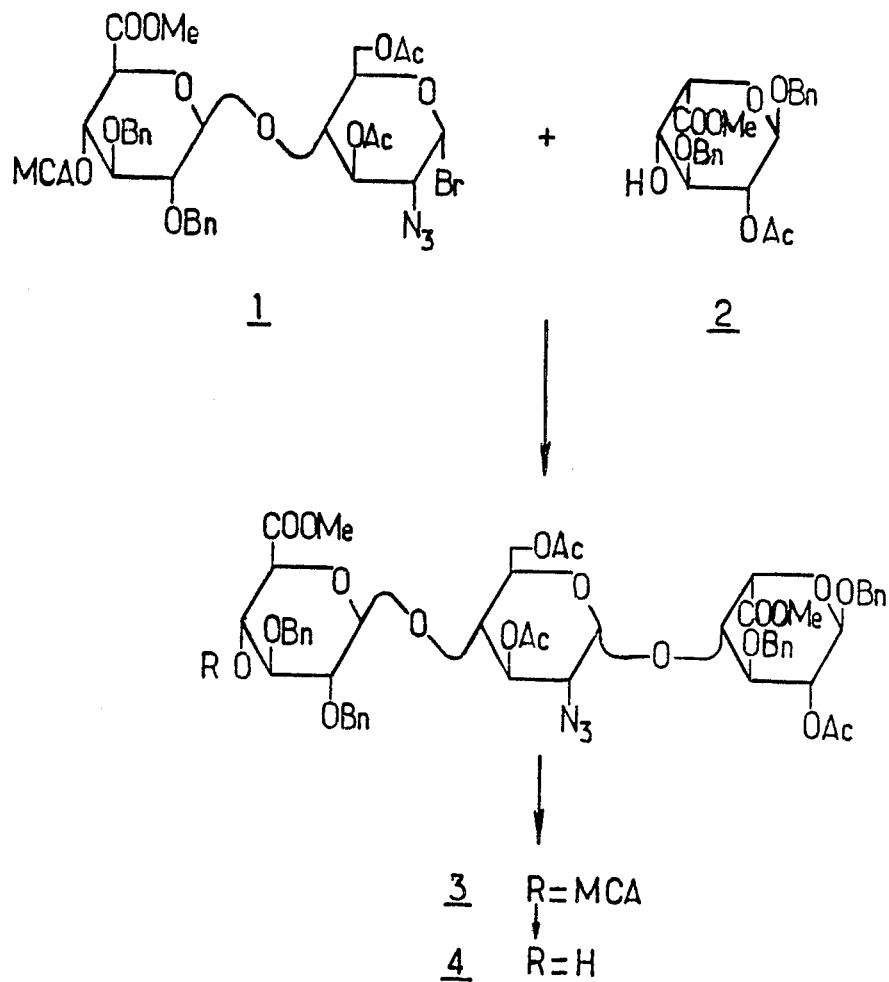
Figure 1:
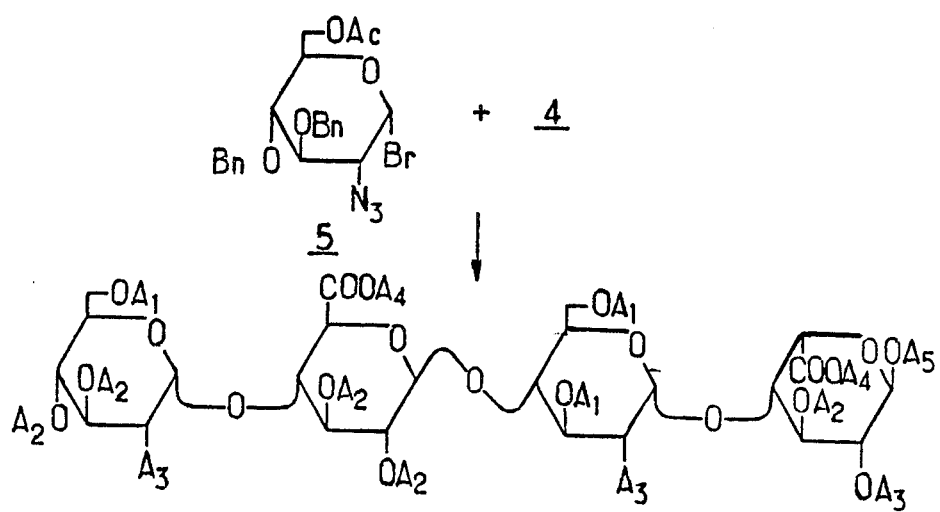
Figure 2:
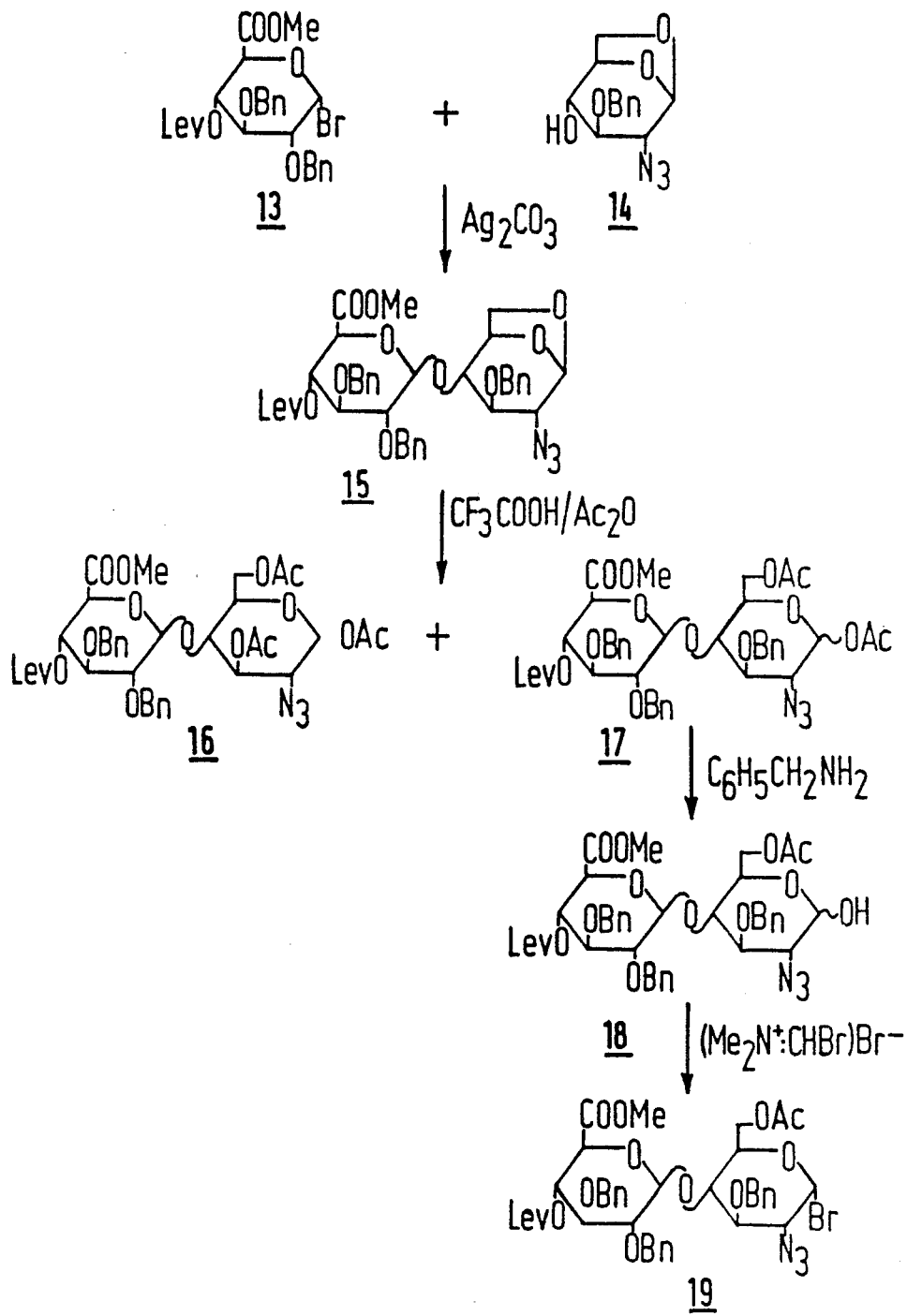
Figure 3:
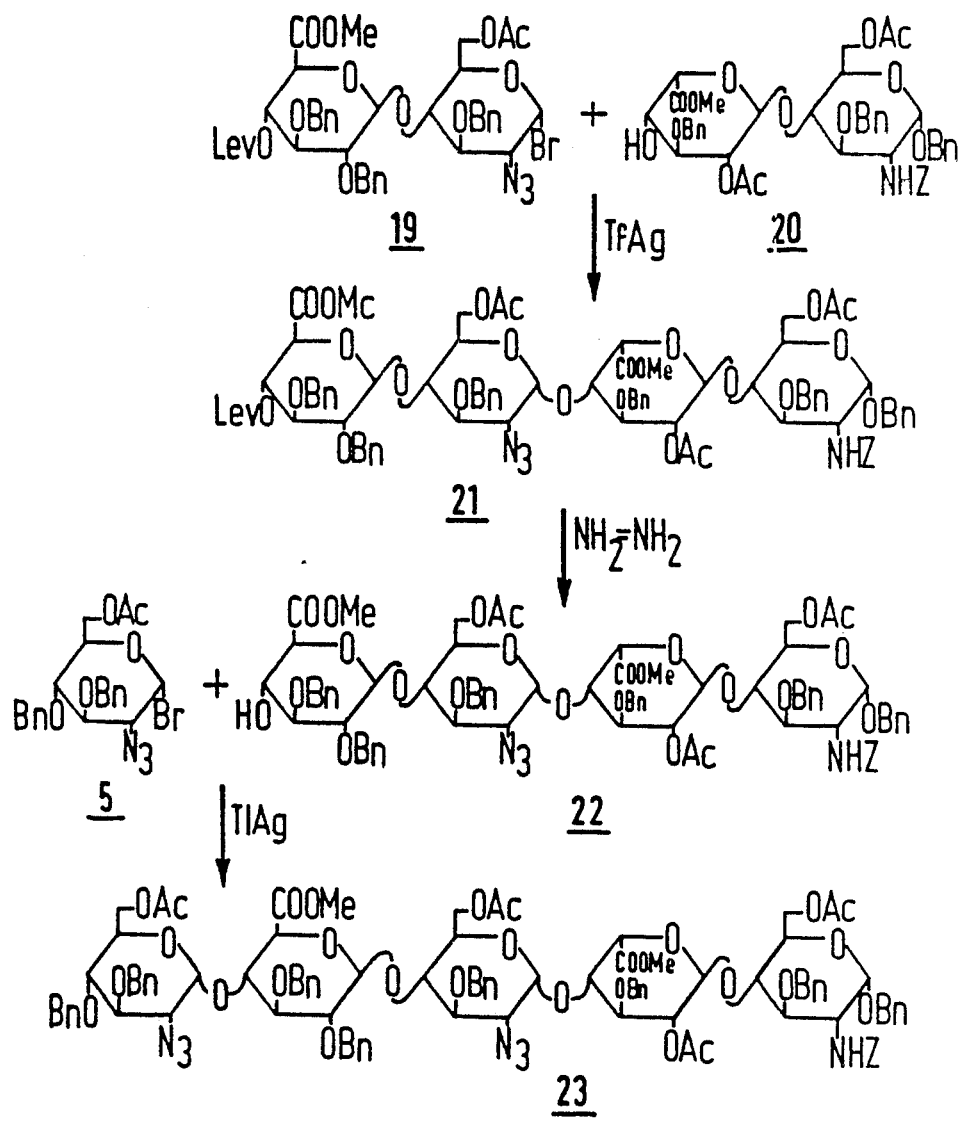
Figure 4:
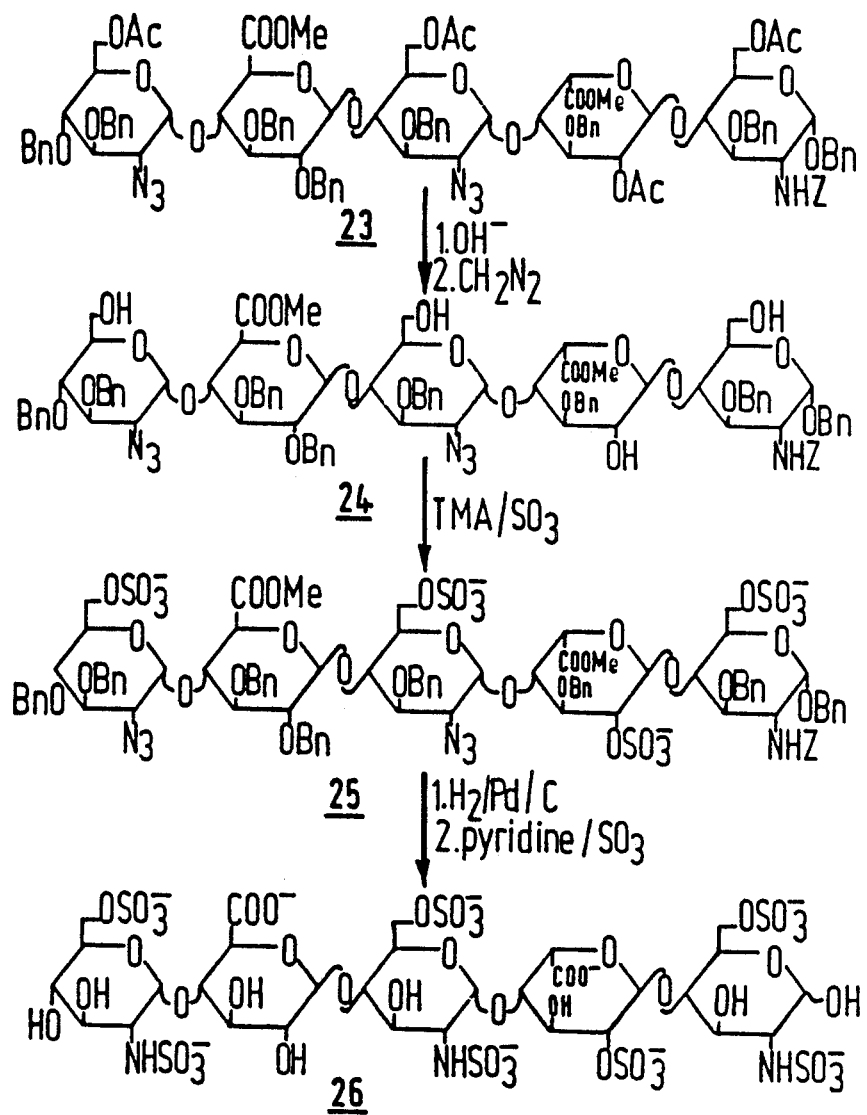

United States Patent [19]
Petitou et al.

[11] Patent Number: 4,801,583
[45] Date of Patent: Jan. 31, 1989

[54] NOVEL OLIGOSACCHARIDES AND THEIR BIOLOGICAL APPLICATIONS

[75] Inventors: Maurice Petitou, Paris; Jean-Claude Lormeau, Maromme; Jean Choay, Paris; Jean-Claude Jacquinet; Pierre Sinay, both of Orleans, la Source, all of France

[73] Assignee: Choay S.A., Paris, France

[21] Appl. No.: 734,445

[22] Filed: May 15, 1985

Related U.S. Application Data

[63] Continuation-in-part of Ser. No. 457,931, Jan. 14, 1983, abandoned.

[30] Foreign Application Priority Data

| Jan. 15, 1982 | [FR] | France | 82 00621 |
| Feb. 1, 1982 | [FR] | France | 82 01575 |
| Feb. 16, 1982 | [FR] | France | 82 02526 |
| May 28, 1982 | [FR] | France | 82 09392 |
| Jun. 22, 1982 | [FR] | France | 82 10891 |
| Jun. 22, 1982 | [FR] | France | 82 10892 |
| Jul. 2, 1982 | [FR] | France | 82 11679 |
| Aug. 6, 1982 | [FR] | France | 82 13804 |
| Sep. 20, 1982 | [FR] | France | 82 15804 |
| Sep. 20, 1982 | [FR] | France | 82 15803 |
| Oct. 27, 1982 | [FR] | France | 82 18003 |
| May 16, 1984 | [FR] | France | 84 07589 |

[51] Int. Cl.$^4$ ............ A61K 31/70; C08B 37/10
[52] U.S. Cl. ................ 514/54; 514/23; 536/18.7/21
[58] Field of Search ........... 536/21, 18.7; 514/23, 514/54

[56] References Cited

U.S. PATENT DOCUMENTS

| 4,207,413 | 6/1980 | Szarek et al. | 536/122 |
| 4,221,907 | 9/1980 | Nair | 536/118 |
| 4,401,662 | 8/1983 | Lormeau et al. | 536/21 |
| 4,435,387 | 3/1984 | Schaub et al. | 536/18.6 |
| 4,440,758 | 4/1984 | Upeslacis et al. | 536/4.1 |

FOREIGN PATENT DOCUMENTS

| 0084999 | 8/1983 | European Pat. Off. | 536/21 |
| 7900910 | 11/1979 | World Int. Prop. O. | 536/123 |
| 8101004 | 4/1981 | World Int. Prop. O. | 536/121 |

OTHER PUBLICATIONS

Fieser et al. *Organic Chemistry*, 2nd Ed., (D. C. Heath and Company Boston), 1950, pp. 229 and 231.

*Primary Examiner*—J. R. Brown
*Assistant Examiner*—Elli Peselel
*Attorney, Agent, or Firm*—Davis Hoxie Faithfull & Hapgood

[57] ABSTRACT

The oligosaccharides of the invention contain or are constituted by a tetrasaccharide enchainment of the formula:

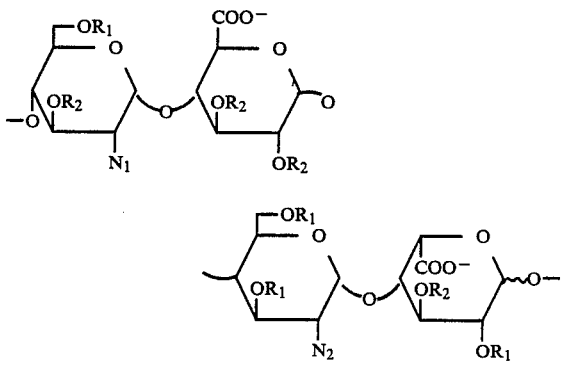

in which $R_1$ represents an organic anion, $R_2$ is identical to $R_1$ or represents a hydrogen atom, $N_1$ and $N_2$ represent a functional amino group.

6 Claims, 5 Drawing Sheets

OLIGOSACCHARIDES AND THEIR BIOLOGICAL APPLICATIONS

This application is a continuation in part of applicant's copending application Ser. No. 457,931, filed Jan. 14, 1983 now abandoned.

BACKGROUND OF THE INVENTION

The invention relates to novel oligosaccharides, their preparation by organic synthesis and their biological applications.

This relates to a development of an invention which gives the subject of U.S. patent application Ser. No. 457,931 of Jan. 14, 1983. In this patent application, a process is described for obtaining by organic synthesis oligosaccharides having the structure of fragments of natural acid mucopolysaccharide chains, and derivatives of these oligosaccharides. It is recalled that the expression "acid mucopolysaccharide" denotes derivatives also currently called glycosaminoglycuronoglycans. These derivatives are formed from oligosaccharides and polysacharides constituting more especially chains of biologically active derivatives such as those of the heparin or heparane-sulfate type. These chains are essentially formed from alternate amino-sugar—uronic acid units, or conversely. In these units, the amino-sugar has more especially a D-glucosamine structure (or a) and the uronic acid a D-glucuronic acid structure (or b) or L-iduronic acid structure (or c).

The great flexibility of the process described in the principal patent application enables the preparation of the desired enchainment of the units, in the desired stereochemistry and with predetermined substitutions. It is thus possible to obtain particularly oligosaccharides constituting anologs of the structure of heparin chain fragments.

These fragments can advantageously include the octasaccharide enchainment ABCDEFGH, obtained previously by applicants by enzymatic depolymerization of structure I.

The oligosaccharides obtained synthetically can also include only one portion of this enchainment, or be constituted by this enchainment.

The letters A to H indicated in the formula, denote, as used in the description, one type of structure, substitutions being identical or different from those of the formula.

As described in this principal patent application, the developed oligosaccharides constitute biological reagents and reference substances which are particularly interesting. They are, in addition, endowed with pharmacological properties conferring on them a utility of great importance as an active principle of medicaments.

Certain of these oligosaccharides are revealed more especially to be active in the field of blood clotting.

Thus, if an anti-Xa activity (measured by the Yin-Wessler titer) has been detectable in a trisaccharide of structure DEF, it is with a pentasaccharide of structure DEFGH that it was possible to demonstrate a very high affinity for anti-thrombin III or ATIII and a very high anti-Xa activity (Yin-Wessler) of at least 2000 units Yin-Wessler/mg.

This product corresponds to the following formula:

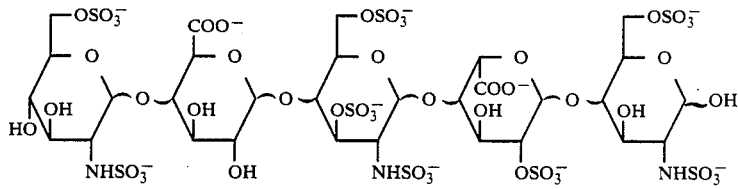

An anti-Xa activity of at least 2000 Yin-Wessler units/mg could be demonstrated.

In continuing their research, the inventors have now observed surprisingly, a sufficiently high activity to permit the exploitation as active principal of an antithrombotic medicament in a group of lower oligosaccharides (this term "lower" being understood with respect to the pentasaccharides).

The extension of this research has led them to develop a specific oligosaccharide group which is shown to be endowed advantageously with a wide therapeutic spectrum.

It is therefore an object of the invention to provide a novel group of oligosaccharides with short chains, whose structure corresponds to that of acid mucopolysacharide chain fragments, or include such fragments.

It is also an object of the invention to provide biological uses of these oligosaccharides as laboratory reagents and as an active principal of medicaments.

GENERAL DESCRIPTION OF THE INVENTION

The oligosaccharides of the invention are characterised in that they comprise from 4 to 12 units selected from among amino sugar and uronic acid units, or conversely, and that they contain a tetrasaccharide enchainment of the structure DEFG, corresponding to the formula II:

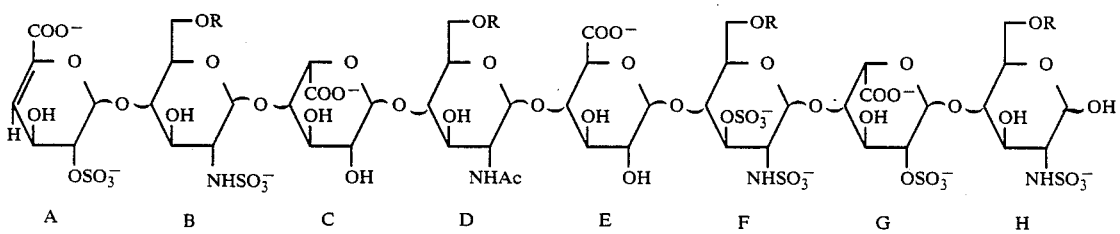

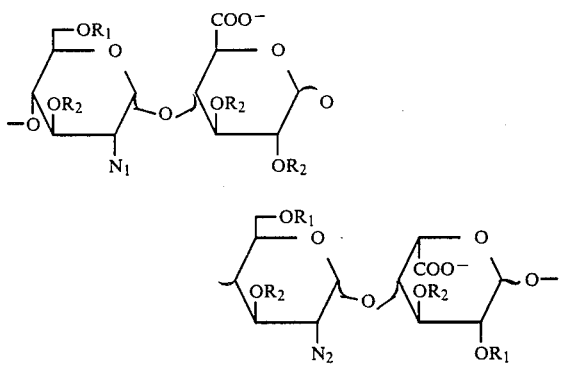

in which:
- the radicals $R_1$, identical or different from one another, represent an inorganic anion, in particular, a sulfate group or a phosphate group,
- $R_2$ has one of the meanings given for $R_1$ or represents a hydrogen atom,
- $N_1$ and $N_2$, identical or different from one another, represent a functional amino group, in particular, in the form of a salt with an inorganic anion as defined above, or substituted by an acyl group —$COR_3$ where $R_3$ represents an alkyl radical.

The studies carried out by applicants in this field have shown the importance of the sequence DEFG which corresponds to the so-called irregular unit present in the natural heparin molecule. This sequence confers on the oligosaccharides and surprisingly and advantageously on the tetrasaccharides DEFG per se, pharmacological properties exploitable in a wide therapeutic field.

In one embodiment of the invention, the above defined oligosaccharides are of the a-b, a-c type, or conversely (it being understood that they comprise the sequence DEFG).

In one group of oligosaccharides, the glycoside chain is constituted outside of the sequence DEFG by a single type of these binary enchainments.

In another group, several of these binary enchainment types are present.

In a modification, these oligosaccharides contain one or several consecutive a or again b, or c units.

In another modification, these oligosaccharides contain one or several neutral sugar units and/or several desoxy-sugars in their structure.

The above constituent units are connected to one another by linkages of the 1-2, 1-3, 1-4, or 1-6 type, and, in the case of oligosaccharides, possessing the structure of fragments of heparin or of heparan-sulfate, comprise linkages

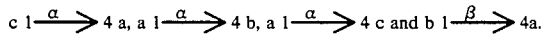

Unexpectedly, the tetrasaccharides of structure DEFG per se are revealed to be endowed with sufficiently important pharmacological properties to permit the use of these products as active principles of medicaments.

The invention is therefore directed, according to a preferred embodiment, at the tetrasaccharides of structure DEFG, of the above formula II, as such.

The economic interest of these products with respect to the higher oligosaccharides can be judged to the extent that they only involve for their synthesis the employment of four units.

A family x of preferred tetrasaccharides by reason of their high anti-Xa activity and their strong affinity for ATIII corresponds to the above formula II in which $R_2$ represents an inorganic anion.

The tetrasaccharides of this family in which $R_2$ represents a sulfate anion, are more especially preferred considering their analogy with natural products.

In this respect, particularly interesting tetrasaccharides contain also sulfate groups for at least certain of their other substituents, or more especially for all of the substituents $R_1$ and/or $N_1$ and $N_2$.

A preferred tetrasaccharide of this type corresponds to the product 12 in Example 3 of formula III:

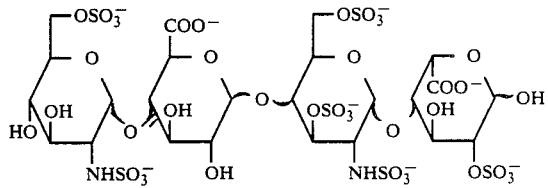

In place of the sulfate groups, other inorganic anions may be present such as the phosphate group.

Another family y of preferred tetrasaccharides, in particular by reason of its fibrinolytic activity comprises a substituent $R_2$ representing the —OH group.

Tetrasaccharides of this type advantageously include sulfate groups for at least certain of their other substitutions $R_1$ and/or $N_1$ and $N_2$. A tetrasaccharide of this group corresponds to the formula IV:

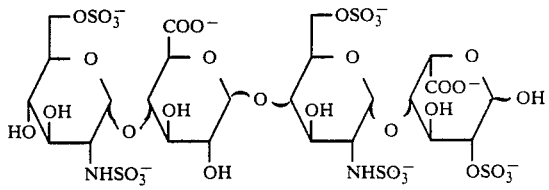

As in the family x, advantageous products contain in place of one or of several sulfate groups, or again of all of these groups, other inorganic anions, such as phosphate anions.

In the various types of tetrasaccharides mentioned above, the various inorganic anions and the carboxyl groups are advantageously present in the form of salts with an inorganic cation in particular the metal cation, especially, an alkali cation such as sodium, magnesium or calcium, or again a cation derived from an nitrogenous organic base, such as triethylammonium.

The preceding arrangements relating to the DEFG enchainment apply also in the case where the sequence is involved in a longer oligosaccharide chain, which can include up to 12 units, as defined above.

In these oligosaccharides, the DEFG sequence can occur at the beginning, be incorporated, or at the end of the chain. Thus, the sequence DEFG occurs in certain of these oligosaccharides at the beginning of the chain, it being understood that the pentasaccharide DEFGH No. 50 concerned above, which is expressly described in the principal patent application, is excluded from the scope of the present invention.

The units which are enchained following the sequence DEFG are as defined above.

Among the oligosaccharides of this type preferred by reason of the interest of their fibrinolytic activity, would be mentioned the tetrasaccharides of the family Y (in which the unit F comprises an —OH group at the 3 position), in which the sequence DEFG is followed by a D-glucosamine unit.

Preferred pentasaccharides of this group comprise those of the structure DEFGH corresponding to the formula V:

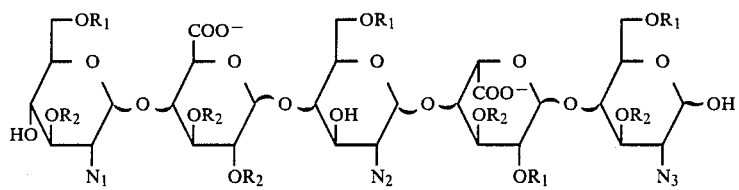

in which the subsituents have the meanings given above, and $N_3$ has the meanings given for $N_1$ and $N_2$.

A preferred pentasaccharide which corresponds to the product 26 of example 4 corresponds to the following formula VI:

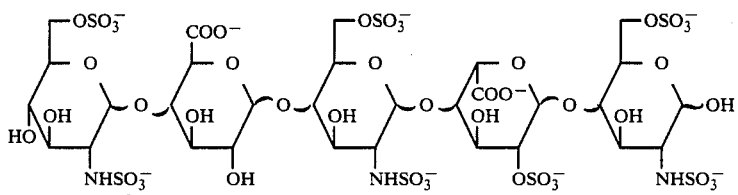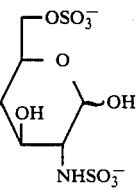

In other oligosaccharides, the tetrasaccharide enchainment DEFG is found incorporated in the oligosaccharide chain.

For other oligosaccharides, this sequence occurs, on the contrary, at the chain end, the foregoing features being applied to these two other groups.

The oligosaccharides of the invention are advantageously prepared by the process of synthesis described in said U.S. patent application.

According to the most general definition of this process, reaction is caused between two compounds constituted or terminated respectively by units of glucosamine structure, in particular D-glucosamine, and units of glururonic acid structure, in particular, D-glucuronic, or iduronic acid, in particular L-iduronic.

One of the amino sugar or uronic acid units is constituted by an alcohol in which the —OH group of the alcohol function occupies any one of the positions 3,4 or 6 in the case of an amino sugar unit and 2,3 or 4 in the case of an uronic acid unit. The other unit then possesses an active anomeric carbon, this is to say including a reactive group capable of establishing with the —OH group of the alcohol the desired —O— glycosylation linkage, in the desired stereochemistry, to form an amino sugar-uronic acid sequence or the reverse.

The groups present on the units employed to constitute the oligosaccharide chain must respond particularly to the following requirements:

the reactive group of the amino sugar or uronic acid unit must be compatible with the protective and/or functional groups present on the units;

the proctective groups of the —OH functions and, as the case may be, of the amino or carboxyl functions, must be compatible between themselves and with the precursor groups of the amino or carboxyl functions when they are present:

the protective and precursor groups must be inert with respect to the glycosylation reaction and with the reactive groups, enabling the positioning in the course of subsequent operations, of given substituents at the various positions, and this, as the case may be, sequentially.

The glycosylation reaction is carried out so as not to alter the structure of the units of these products and the nature of the various substituents present.

The above glycosylation step is repeated so as to obtain the desired chain length.

To be able to carry out this elongation of the glucid skeleton, amino sugar or uronic acid units are then employed including temporary protective groups, that is to say, groups capable of selectively blocking a position of the amino sugar or uronic acid unit intended to take part in a further glycosylation reaction. These are groups which can be removed in the presence of other groups present on the units by recreating an alcohol.

After development of the desired glucidic skeleton, the chain formed is subjected to one or several chemical reactions in order to introduce a given type of functional group or successively, several types of groups and then to form, if desired derivatives of these functional groups.

To introduce specific substitutions, that is to say predetermined substitutions at given positions, use is made with advantage of starting material containing several types of protective groups, namely (1) one or several semi-permanent groups and (2) one or several permanent groups.

The semi-permanent groups are removable in the first place and enable the introduction of the desired functional groups at the positions that they occupy. The permanent groups are on the contrary capable of maintaining the protection of the —OH radicals during the introduction of the functional groups in place of the semi-permanent groups.

The starting materials of the amino sugar type contain in addition at the 2 position, a nitrogen group enabling the maintenance of the presence of a nitrogen function during the operations employed in the process. This nitrogen group is advantageously constituted by groups such as $—N_3$ or $—NHCOO—CH_2—C_6H_5$, or any other group constituting a percursor of an amino function or of an amino derivative, particular, —NH—SO$_3$— or —NH—acyl, or especially —NH—COCH$_3$.

As for the carboxyl functions of the uronic acids, they are blocked by groups inert with respect to the reactions employed for the replacement of the protective groups and removable at the end of the synthesis to release the carboxyl groups, as the case may be, for the salification purposes. These protective groups of the carboxyl function are selected advantageously among alkyl radicals or aryl radicals.

These dispositions are employed to prepare the oligosaccharides of the invention.

As regards more particularly the obtaining of the sequence DEFG, reaction is advantageously, caused of a halogenide, more especially the bromide of a disaccharide of structure EF whose synthesis is described in the principal patent application with an alcohol of a unit of structure G.

The disaccharide EF includes a temporary group at the 4 position of the E unit. This group is advantageously selected from among acyl groups in particular, acetyl or chloroacetyl.

The condensation reaction is carried out in a solvent, more particularly in an organic solvent, particularly in dichloromethane or dichlorethane.

Advantageously, a catalyst is used, in general a silver or mercury salt, for example, silver trifluoromethane sulfonate, commonly called silver triflate, silver carbonate, silver oxide, mercuric bromide or mercuric cyanide. A proton acceptor such as sym-collidine is also used in the same way as a trapping agent for the water possibly present and/for the hydrohalogenic acid formed, for example 4 Å molecular sieves.

Study of the reaction conditions shows that it is appropriate to operate at ambiant temperature or again at a lower temperature which can reach 0° C. or less, under an atmosphere of inert gas such as nitrogen or argon.

Formation of the trisaccharide chain of structure EFG, the temporary group of the unit E is removed by conventional techniques to recreate the —OH group. The latter is then engaged in a glycosylation reaction with the halogenide, more especially the bromide of the unit of structure D.

As regards the development of the structure DEFGH of formula V, recourse is advantageously had in a modified embodiment, to a condensation reaction of a halogenide of unit E, including a temporary group at the 4 position, such as the levinoyl group or the like, and an achohol of structure F unit. The 1 and 6 positions of this alcohol are advantageously blocked by a 1,6-anhydro bridge, which will be opened after the glycosylation reaction.

The disaccharide sequence of structure EF formed, after treatment in order to activate the anomeric carbon of unit F, by introducing, for example a halogenide, particularly a bromide is employed in a condensation reaction with an alcohol of structure GH the tetrasaccaride formed is then treated so as to recreate an alcohol group at the 4 position of the E unit, then condensed with a reactive derivative of a unit D, particularly a halogenide, in particular a bromide.

To prepare more especially, the tetrasaccharides of formula II and the pentasaccharides of formula V in which R$_1$ represents the sulfate group, R$_2$ a hydroxyl group and N$_1$ and N$_2$ are identical and represent sulfate groups, starting materials are employed including the following groups.

The protective groups of the —OH radicals of these various units intended to be sulfated are protected by acyl groups, in particular, acetyl, while the —OH radicals intended to be liberated at the end of the synthesis are protected by a permanent group such as the benzyl group.

The 2 positions of the amino sugar units are substituted by groups such as N$_3$ or NH—COO—CH$_2$—C$_6$H$_5$ and the 6 positions of the uronic acid units are occupied by carboxyl groups protected by an alkyl radical, in particular methyl.

The functionalisation of the tetrasaccharide formed, that is to say of sequential introduction of specific substition, is then carried out according to the instructions given in the principal patent application.

This set of conditions enables the functionalisation step to be carried out, for example as follows:

The sulfate groups are first of all introduced selectively after having removed the —0 acetyl blocking groups. This reaction is performed so as not to affect the benzyl groups and the nitrogen and carboxyl groups present.

In this respect, a saponification reaction is advantageously performed by means of a strong base such as soda.

This reaction is preferably performed at a temperature below ambiant and more especially in the vicinity of 0° C.

The product resulting from the hydrolysis is subjected to the action of an alkylating agent in order to introduce, onto the carboxyl group the protective alkyl groups which become eliminated during hydrolysis.

By reaction with a sulfation agent, introduction is made of sulfate groups at the positions liberated by the hydrolysis and left free after the action of the alkylation agent.

Satisfactory reaction conditions for conducting the sulfation comprise the employment of a sulfation agent, such as the trimethylamine/SO$_3$-complex. This reaction is advantageously carried out in a solvent, more especially in a solvent such as dimethylformamide. Preferably, it is performed at a temperature above ambiant, generally in the vicinity of 50° C., which corresponds to a reaction time of about 12 hours.

After the introduction of the sulfate groups onto the alcohol functions, the liberation of the —OH groups blocked by the benzyl radical follows.

The removal of benzyl groups is advantageously carried out by catalytic hydrogenation under conditions compatible with the maintainance of the sulfate groups and the transformation of the nitrogen groups into amine functional groups.

The operation is preferably carried out under hydrogen pressure in the presence of a catalyst of the Pd/C type.

This reaction is advantageously carried out in an organic medium, in particular alcohol, to which water has been added.

To obtain the hydrogenation of the precursor nitrogen groups and the removal of the protective radicals of the —OH groups, the reaction is advantageously performed over a period of about 3 to 4 days.

As already indicated, the amine functional groups are in a form of derivatives of the N-acetyl or N-sulfate type, in the biologically active molecules concerned.

To form N-acetyl groups, the product resulting from the hydrogenation reaction is subjected to the action of an acetylation agent. In this respect, acetic anhydride constitutes a particularly suitable agent.

To perform this selective acetylation reaction without affecting the other substituents present on the unit, it is convenient, particularly, to operat a basic pH, in particular in the vicinity of 8 in an aqueous medium.

It may also be desired to form N-sulfate groups, which can be carried out by means of a sulfation agent of the above-indicated type. Ph's higher than 9, advantageously of the order of 9–10, are used for the sulfation.

After the sulfation reaction, the addition of a strong base enables the carboxyl groups to be liberated.

The products formed can easily be salified by means of exchange resins with suitable cation. In natural products, the cation in particular is constituted by sodium. Advantageously exchange resins with sodium cations are used.

It is also possible to form potassium, lithium magnesium, calcium salts. A proton exchange resin is then used, then the acid formed is neutralised with the cation base.

The invention is directed also at oligosaccharides constituting intermediates in the various steps of the above-defined synthetic process.

Study of the pharmacological actions of the oligosaccarides of formula I containing the sequence DEFG, or constituted by this sequence has permitted the demonstration of their therapeutic interest.

They exert, in particular, an activity on fibrinolysis by increasing the activator level of circulating plasminogen and by sensitizing the clot to lysis.

Studies carried out have been done on various experimental models by the technique described by Vairel et al. Ann. Pharmaceutiques Françaises, 1983, 41, No. 4, p. 339–353.

Thus, 15 min after intravenous injection in a rabbit (anesthesia 20 min before administration) of 0.25 mg of oligosaccharides per kg, an increase is observed in the activator level of plasminogen in the circulating blood.

With, for example, the tetrasaccharide DEFG formula III, an average increase is observed of the areas of lysis of 17.80, whilst with physiological serum used as a control, a decrease of 0.5 is noted. A similar increase to that of the tetrasaccharide is obtained with the pentasaccharide of structure VI.

Work carried out on the oligosaccharides of the invention, in which the structural unit F includes a $-SO_3$ groups at the 3 position, have revealed an anti-Xa activity distinctly higher than that of heparin and a strong affinity for AT-III. In the case, for example, of the tetrasaccharide of formula III (product No. 11) the anti-Xa activity measured with a chromogenic substrate is 600 anti-Xa units/mg (modified method of Teien A.M. and Lie, Thrombosis Research No. 10, 1987, 388–410).

The therapeutic efficiency of these products has been studied with well-defined animal models in order to determine their anti-thrombotic power under known pathological conditions.

With the modified stasis model of the rabbit (see Throm and Hemost. 46, (1) 117, 1981 by Anderson et al.), the following results were obtained.

To rabbits intravenously were administered 50 μg/kg of products dissolved in a saline solution (in the proportion of 100 μg/kg). Five minutes before the addition of a thrombogenic agent.

The thrombogenic agent is constituted either by rabbit serum, or by PCC/RVV agent (concentrate of a pro-thrombin and venin complex of Rupper viper). The stases of the right and left jugular veins were graduated on a scale from 0 to 10.

Complete protection was observed (quotation 0) against the thrombogenic effects induced by rabbit serum and partial protection with respect to the thrombogenic agent PCC/RVV (quotation 5), the control having a quotation of 10.

The oligosaccharides of the invention in which the F structural unit comprises, at the 3 position, an —OH group, do not appear to be endowed with activity with respect to the Xa factor, and hence have a greater specificity than the group of oligosaccharides with an $-SO_3^{31}$ group at the 3 position of the structural unit F with respect to fibrinolytic activity.

Toxicological studies of the products of the invention have shown their innocuousness which renders them valuable for the development of medicaments.

The invention hence also relates to pharmaceutical preparations which contain said oligosaccharides.

It relates more particularly to pharmaceutical preparations devoid of pyrogenic substances, containing an effective amount of active principles in association with pharmaceutical excipients.

It is aimed particularly at compositions in which the pharmaceutical vehicle is suitable for oral administration. Suitable forms of administration of the invention for oral use may advantageously be gastroresistant capsules, tablets or lozenges, pills, or again, presented in liposome form.

Other pharmaceutical compositions comprise these oligosaccharides in association with suitable excipients for administration rectally. Corresponding administrative forms are constituted by suppositories.

Other forms of administration of the invention are constituted by aerosols or pommades.

The invention also relates to injectable, sterile or sterilizable pharmaceutical compositions for administration both intravenously and intermuscularly, or subcutaneously. These solutions advantageously contain products of the family x in the ratio of 1,000 to 100,000 u (Yin-Wessler)/ml of oligosaccharides, preferably from 5,000 to 50,000, for example, 25,000 u/ml, when these solutions are intended for injection subcutaneously. They can contain, for example, from 500 to 10,000 particularly 5,000 u/ml of oligosaccharides, when they are intended for injection intravenously, or by perfusion.

Advantegeously, such pharmaceutical preparations are offered in the form of ready-for-use, discardable syringes.

The invention also relates to pharmaceutical compositions containing said oligosaccharides, in association with another active principle.

The pharmaceutical compositions of the invention are particularly adapted for the control (preventive or curative) of certain steps of blood coagulation in man or animal, particularly in the case where the patient is subject to risks of hypercoagulability, resulting particularly from surgical operations, atheromatous processes, tumor development and disorders of clotting by bacterial or enzymatic activators, etc.

In order to illustrate the invention, there is indicated, below, an example of the posology usable in man with the products of the family x; this posology comprises, for example, the administration to the patient of 1,000 to 25,000 u, (Yin-Wessler) subcutaneously, once to thrice daily, according to the level of the clotting risks or the thrombotic condition of the patient, or 1,000 to 25,000 u/24 hours, intravenously, in discontinuous administrations at regular intervals, or continuous by perfusion or again, 1,000 to 25,000 u (thrice weekly) intra-muscularly or subcutaneously) these titers are expressed in Yin-Wessler units). These doses can naturally be adjusted for each patient according to the results and blood analyses carried out previously, the nature of the infections from which he is suffering and, in general, his state of health.

In the case of products of family y, particularly pentasaccharides of formula VI, 1 to 100 mg/day are administered according to the state of the patient and the pharmaceutical form used.

Besides pharmaceutical compositions containing the oligosaccharides as such, the invention is also directed at pharmaceutical compositions containing at least one oligosaccharide as defined above, conjugated, by a covalent linkage, to a soluble support, or to an insoluble support advantageously by means of the reducing terminal sugar.

Conjugates fixed to preferred soluble supports are constituted more especially by conjugated oligosaccharides AT-III, comprising a sequence DEFG of formula II, more especially a sulfate group. Such products constitute particularly advantageous medicaments in the prevention of thromboses, in the case of AT-III deficits.

Other preferred conjugates with soluble supports are formed from an oligosaccharide of the general formula II, fixed to a vehicle such as a protein, particularly polylysine, or bovine albumin serum.

These products are usable as immunogens themselves sources of circulating antibodies produced in vivo or of monoclonal antibodies, cloned in vitro by suitable techniques.

In other preferred conjugates, the oligosaccharides of the invention are conjugated to insoluble support. Advantageously, the above conventional supports are used. These conjugates when they contain a DEFG sequence according to the above family x, are useful as immunoabsorbants, for example, for a purification of high specificity of AT III and for its dosage or for the development, by fixation on biocompatible polymers of novel, athrombotic hemocompatible polymers.

In addition, the complexes resulting from the affinity of AT III for the oligosaccharides of the invention, contain the sequence DEFG of the family x, entering also within the scope of the invention.

The invention is directed also at the application of the oligosaccharides concerned in nuclear medicine, as radiopharmaceutical products. These products are then marked by tracers selected from among those currently used in this field, and particularly by means of technetium 99m.

For this purpose, the technetium 99m obtained from commercial generators, in the form of sodium pertechnetate of non-reactive valence 7, is converted into reduced technetium of valence 4, which is the most reactive form of technetium. This transformation or conversion is carried out by means of a reducing system effected from tin salts (stannous chloride), iron salts (ferrous sulfate), titanium salts (titanium trichloride) or other salts.

The majority of the time, this simple reduction of technetium is sufficient under given pH conditions, to effect the fixation of technetium to the molecules concerned.

It is possible to use the products of the invention, which constitute in a way a support, at doses of the order of 100 to 200 u Yin-Wessler.

For developing these radiopharmaceutical reagents, it is possible to operate in accordance with the method of P.V. KULKARNI et al in The Journal of Nuclear Medecine 21, No. p, 117–121.

The thus marked products are advantageously used in the in vivo tests for the detection and the extension diagnosis of thrombosis and of thrombotic states.

The oligosaccharides of the invention can also be used for the determination of the specificity of numerous enzymes involved in the metabolism of glycosaminoglucuronoglycans.

Other advantageous features of the invention will appear in the examples which follow and by refering to FIGS. 1 to 5 illustrating the products employed in the syntheses described.

In these Figures, the numerical references of formulae are used also in the examples to denote the same products.

The abbreviations used in these formulae have the following meanings:

Ac: an acetyl group; Me: methyl; Bn: benzyl; Lev: levinoyl; MCAO: monochloroacetyl; and Z: a benzyloxycarbonyl group

EXAMPLE 1

Preparation of the trisaccharide 3 of structure EFG viz. benzyl-O

[methyl-2,3-di-O,benzyl-4-O-chloroacetyl-β-D-glucopyranosyluronate-(1→4)-O-(3,6-di-O-acetyl-2azido-2-desoxy-α-D-glucopyranosy)-(1→4)-O-[methyl-2-O, acetyl-3-O-benzyl-α-L-idopy-ranosiduronate]

The synthesis of the trisaccharide 3 is carried out by condensation of a halogenide structure EF and alcohol of structure G. These agents numbered respectively 1 and 2 in the description correspond respectively to the products 20 and 147 described in U.S. patent application Ser. No. 457,931 of Jan. 14, 1983 in the name of applicant.

This condensation step is carried out as follows:

A solution of halogenide 1 (738 mg; 0.92 mmole) and of alcohol 2 (428; 1 mmole) in anhydrous dichlorethane (15 ml) is shaken at 20° C. in the presence of powdered 4 Å molecular sieve. Then collidine (150 μl), then silver triflate (262 mg; 10 mmole) are added. After one hour at −20° C., the reaction mixture is diluted with dichloromethane then filtered. The organic phase is washed (KHSO$_4$) (10% water), dried, (Na$_2$SO$_4$) and concentrated to dryness. The foam obtained (1.07 g) is chormatographed on silica gel (toluene/ethyl acetate 4/1; v/v) thus yielding the trisaccharide 3 pure (699 mg; 63%) in the form of a white foam.

[α]$_D$: +25° (c 1.4; chloroform).

EXAMPLE 2 preparation of a tetrasaccharide 6 of structure DEFG, namely benzyl O-(6-O-acetate-2-azido-3,4-di-O-benzyl-2-desoxy-α-D-glucopyranosyl)-(1→4)-O-[methyl 2,3-di-O-benzyl-β-D-glucopyranosyl-uronate]-(1→4)-O-(3,6-di-O-acetate-2-azido-2-desoxy-α-D-glucopyranosyl)-(1→4)-O-(methyl 2-O-acetyl-3-O-benzyl-α-L-idopyranosiduronate)

This synthesis is carried out by condensation of a halogenide 5 of structure D with an alcohol 4 corresponding to the trisaccharide 3, whose —OH group at the 4 position of the E unit has been unblocked.

There are described successfully:

(a) obtaining the trisaccharide 4 from the trisaccharide 3.

(b) condensation of 4 with the halogenide 5.

Step a:

Trisaccharide 3 (699 mg; 0.55 mmoles), is dissolved in a mixture of lutidine (3.8 ml) and, acetic acid (1.25 ml). Methanol is then added, followed by hydrazine dithiocarbonate solution obtained by the method described by Van Boeckel and Beetz in Tetrahdron letters 24 (1983) 3775-3778. After two hours at ambient temperature the solution is diluted by the addition of dichloromethane (200 ml), then washed (NaHCO$_3$ saturated, water KHSO$_4$ 10%, water) dried (Na$_2$SO$_4$) and concentrated to dryness. The pure product (530 mg; 83%) is obtained after chromatography on silica gel (toluene/ethyl acetate: 2/1 v/v).

$[\alpha]_D$: +29° (c 1.29; chloroform).

Analysis:

|   | Calcul for C$_{54}$H$_{11}$O$_{20}$N$_3$ | Found |
|---|---|---|
| C | 60.50 | 60.46 |
| H | 5.74 | 5.74 |
| N | 3.92 | 4.11 |

Step b:

A solution of alcohol 4 (494 mg; 0.455 mmole) in dichloromethane and halogenide 5 (1.096 g; 2.2 mmoles) is treated with silver triflate (632 mg) in the presence of symcollidine (360 μl) as is described for the synthesis of the compound 3. After purification on the silica gel column (chloroform gradient→chloroform ethyl acetate; 20/1, v/v) the pure derivative 6 is obtained (595 mg; 89%).

$[\alpha]_D$: +43° (1.27; chloroform).

Analysis:

|   | Calcul for C$_{76}$H$_{84}$O$_{24}$N$_6$ | Found |
|---|---|---|
| C | 61.61 | 61.57 |
| H | 5.71 | 5.76 |
| N | 5.67 | 5.61 |

EXAMPLE 3

Preparation of the tetrasaccharide 11 of structure DEFG, namely the sodium octasalt of O-(2-desoxy-6-O-sulfo-2-sulfamido-α-D-glucopyranosyl)-(1→4)-O-(β-D-glucopyranosyluronate)-(1→4)-O-(2-desoxy-3,6-di-O-sulfo-2-sulfamido-α-D-glucopyranosyl)-(1→4)-O-2-O-sulfo-α-L-idopyranuronate The tetrasaccharide is obtained by sequential deblocking of —OH groups and introduction of the desired groups onto the tetrasaccharide 6.

The successive steps employed are as follows:
1. Liberation of the —OH groups blocked by the acetate groups;
2. Formation of the sodium salts of the sulfate groups;
3. Formation of the sodium salts of the carboxyl groups;
4. Liberation of the —OH groups blocked by benzyl groups and transformation of the azide groups into amino groups,
5. esterification of the amino functions.

These steps are carried out as follows

1. Passage from —OAC to —OH leading to the tetrasaccharide of 7.

The derivative 6 (0.340 g) is dissolved in a mixture of methanol (30.5 ml) chloroform (3,5 ml) and water (4.25 ml). 5N soda is then added (4.25 ml). After 4 hours at ambient temperature, chloroform (3×10 ml) is then added, then hydrochloric acid (8N; 8 ml). After decantation, the chloroform phase is separated. The aqueous phase is washed with chloroform (3×10 ml). The chloroform phases are combined and dried (Na$_2$SO$_4$). The residue obtained after concentration to dryness is methylated with diazomethane, then it is chromatographed on silica gel column eluted by a gradient (dichloromethane→dichloromethane/ethyl acetate group 1/1 v/v). The compound 7 is obtained (0.173 g; 57%).

$[\alpha]_D$: 14° (c 1; chloroform)

Analysis:

|   | Calcul for C$_{68}$H$_{76}$O$_{21}$N$_6$ 0.5 H$_2$O | Found |
|---|---|---|
| C | 61.68 | 61.62 |
| H | 5.93 | 5.34 |
| N | 6.34 | 6.31 |

2. Passage from —OH to —O-SO$_3$Na leading to the tetrasaccharide 8.

The compound 7 (117 mg; 0,068 mmoles) is dissolved in anhydrous dimethylformamide (3 ml), then it is sulfated overnight at 50° C. in the presence of trimethylamine/SO$_3$ (123 mg). The reaction mixture is then diluted by the addition of a methanol chloroform mixture (1/1; v/v; 3 ml) then it is chromatographed on a Sephadex LH 20 column, equilibrated in chloroform/methanol (1/1; v/v). The product obtained is used directly for the preparation of 9.

3. Passage from COOMe to COONa resulting in the tetrasaccharide 9.

The compound 8 (357 mg; 0.207 mmole is dissolved in a methanol mixture (8 ml) and water (2 ml), then soda (5N; 1.2 ml). After three hours of reaction, the reaction mixture is passed through a Dowex 50-H$^{30}$ resin column, equilibrated in a methanol/water (8/2; v/v) mixture. The eluate is passed through a Dowex 50-Na$^+$ column, equilibrated in the same solvent. After evaporation to dryness, product 9 is obtained pure (0.267 g) following chromatography on a silica gel (30 g; ethyl acetate/pyridine/acetate acid/water; 160/77/19/42; v/v/v/v), followed by passage over the ion exchanger Sephadex SPC 25 (18 g) equilibrated in Na+ form in a methanol/water mixture (8/2; v/v).

$[\alpha]_D$: 5.50 (1.025, methanol).

4. Passage from —OBn to —OH and from —N$_3$ to —NH$_2$ resulting in tetrasaccharide 10.

The compound 9 (256 mg; 0.147 mmole) is dissolved in a methanol/water mixture (9/1; v/v; 10 ml) then hydrogenated in the presence of a catalyst (Pd/C 10%; 130 mg) for 5 days. The catalyst is replaced by fresh catalyst and then the reaction is continued for 4 days. The U.V spectrum of the product then shows the absence of benzyl derivatives. The product obtained (0.17 g) is sent directly into the preparation of 11.

5. Passage from —NH$_2$ to —NHSO$_3$Na resulting in tetrasaccharide 11.

To a solution of 10 (0.17 g; 0.152 mmoles) in water (10 ml) is added little by little, the complex pyridine/SO$_3$ (140 mg; 0.75 mmole) whilst keeping the pH at 9.5 by the addition of 2M soda. A fresh addition of sulfating complex is made after one hour (70 mg) and one night (70 mg). The reaction mixture is then deposited at the top of a Sephadex G 50 column (300×2.5 cm) eluted with 0.2M sodium chloride. The product is then absorbed at the top of a Biore AG 1×2 resin column (1.6×10 cm) in Na+ form eluted with a sodium chloride gradient (0.5M→3M). The fractions containing the product were combined. The salts were removed by chromatographyon Sephadex G-25 (100 mg). The product was then freeze-dried (111 mg; 54%).

$[\alpha]_D$: +46 (c 0.85; water)

By employing in the preceding steps a unit G including —OCH$_3$ group in place of the —OBn group on the anomeric carbon atom, the tetrasaccharide 12 was obtained.

In the table below are indicated the meanings of the substituents A$_1$ to A$_5$ of formula 5 given on sheet I for compounds 6 to 12.

|    | A$_1$  | A$_2$ | A$^3$    | A$_4$ | A$_5$ |
|----|--------|-------|----------|-------|-------|
| 6  | Ac     | Bn    | N$_3$    | Me    | Bn    |
| 7  | H      | Bn    | N$_3$    | Me    | Bn    |
| 8  | So$_3$Na | Bn  | N$_3$    | Me    | Bn    |
| 9  | So$_3$Na | Bn  | N$_3$    | Na+   | Bn    |
| 10 | So$_3$Na | H   | NH$_2$   | Na+   | H     |
| 11 | So$_3$Na | H   | NHSO$_3$Na | Na+ | H     |
| 12 | So$_3$Na | H   | NHSO$_3$Na | Na+ | CH$_3$ |

EXAMPLE 4

Preparation of the pentasaccharide 27 of structure DEFGH, including a unit F with at the 3 position, a group —OH, or
O-(2-desoxy-6-O-sulfo-amino-α-D-glucopyranosyl)-(1→4)-O-(β-D-glucopyranosyluronate)-(1→4)-O-(2-desoxy-6-O-sulfo-2-sulfo-amino-α-D-glucopyranosyl)-(1→4)-O-(2-O-sulfo-α-L-ido-pyranosyluronate)-(1→4)-2-desoxy-6-sulfo-2-sulfo-amino-D-glucopyranose.

For the preparation of this pentasaccharide, recourse is had to the following steps (a)-(j).

(a) Preparation of disaccharide 15 of structure EF—namely,
1,6-anhydro-2-azido-3-O-benzyl-2-desoxy-4-O-(methyl 2,3 di-O-benzyl-4-O-levulinyl-D-glucopyranosyluronate-β-D-glucopyranose.

A solution of the alcohol 14 (4.7 g: 17 mmoles) in anhydrous dichloromethane (40 ml) is subjected to stirring, protected from light and moisture, in the presence of silver carbonate (4.3 g 15 mmoles) of 4 Å molecular seive in powder form and drierite. After one hour of stirring, a solution of the halogenide 13 (5.7 g; 10.3 mmoles) in dichloromethane (20 ml) is added at 0° C., drop by drop. After five days of reaction, the reaction mixture is diluted with dichloromethane, and is filtered and concentrated to dryness. By chromotography on silica gel, the un-reacted alcohol is recovered (eluted by a hexane/ethyl acetate mixture; 2/1; v/v) and also the disaccharide 15 (eluted by a hexane/ethyl acetate mixture; 4.1 v/v). The disaccharide 15 is crystallised by means of an ethyl acetate/hexane mixture; 4.1 g 53%).

MP: 93°-94° C.

$[\alpha]_D$: +5° (c 1; chloroform)

(b) Opening of the 1,6-anhydro bridge of the unit of structure F.

A mixture of the disaccharide 15 (4.5 g acetic anhydride (42 ml) and trifluoroacetic acid (12 ml) is subjected to stirring at ambient temperature for about 14 hours. After evaporation, to dryness, the residue obtained is chromatographed on silica gel by means of a hexane/ethyl acetate mixture. The derivative 17 (2.7 g; 52%) is obtained, as well as the 3-O-acetyl derivative 16 (1.4 g) is obtained.

$[\alpha]_D$: +15° (c 1.1; chloroform)

(c) Transformation of the group —OAc at the 1 position of the unit of structure F into —OH.

A mixture of the compound 17 (2.46 g; 2.9 mmoles) ether (120 ml) and benzylamine (12 ml) is subjected to stirring at ambient temperature, for 6 hours. After dilution with ether (700 ml), the solution obtained is washed with cold 1M HCl, then with water and concentrated to dryness. The syrup obtained is chromatographed on silica gel by means of a chloroform/ethyl acetate mixture (2/1 (v/v)). In this way, the derivative 18 (2.047 g; 84.5%) in the form of a white foam, is obtained.

$[\alpha]_D$: +21.30° (c 1.6; chloroform)

(d) Bromidation of the 1 position of the unit of structure F.

To a solution of the derivative 18 (162 mg; 0.2 mmole) in dichloromethane (5 ml) is added at 0° C. sym-collidine (320 μl) then N,N-dimethyl formiminium bromide freshly prepared (Vilsmeier reagent). After 6 hours reaction, a further addition of Vilsmeier reagent follows, then it is left for about 14 hours at 4° C. After dilution with dichloromethane, washing with cold water, drying and evaporation, the residue is chromatographed rapidly on silica gel by means of a dichloromethane/ethyl acetate mixture (5/1 (v/v)). The compound 19 (83 mg; 4 7.5%) is obtained which is immediately employed in the glycosylation reaction.

(e) Glycosylation reaction resulting in a tetrasaccharide enchainment.

A solution of the halogenide 19 (360 mg; 0.414 mmole) and alcohol 20 (710 mg; 0.82 mmole) in dichloromethane (10 ml) is subjected to stirring, at −20° C. in the presence of 4 Å powder molecular sieve. Sym-collidine (66 μl) and then silver triflate (177 mg; 0.45 mmole) are then added. The same amounts of sym-collidine and silver triflate are added after 2 hours reaction, then the mixture is left to return to 0° C. After 14 hours approximately, a further addition of triflate and collidine follows. The reaction is terminated after 48 hours. After dilution with dichloromethane, the reaction mixture is filtered. The solution is washed (KHSO$_4$ 10%; water), dried (Na$_2$SO$_4$) and concentrated to dryness. The syrup obtained (1 g) is chromatographed on silica gel (dichloromethane/ethyl acetate 4.5/1; v/v), giving the desired derivative 21 (287 mg; 42.5%), as well as the unreacted alcohol 20 (990 mg; 55%).

$[\alpha]_D$: +45.60° (c 1.78; chloroform).

(f) Transformation of the group —OLev in the 4 position of the E unit into —OH group.

To a solution of the compound 21 (272 mg; 0.165 mmole) in pyridine (0.9 ml) is added 1M solution of hyrazine hydrate in pyridine acetic acid (3/2; v/v). After five minutes, the mixture is diluted with dichloromethane and then the solution is washed (KHSO$_4$ 10%, water, saturated NaHCO$_3$, water), dried (Na$_2$SO$_4$) and concentrated to dryness. The solid residue obtained (259 mg) is subjected to chromatography on a silica gel column. A hexane/ethyl acetate mixture: 1/1 (v/v) is used. In this way, the derivative 22 (219 mg; 86%) is obtained.

$[\alpha]_D$: +51.50° (1.05; chloroform).

(g) Glycosylation reaction with the tetrasaccharide 21 and the monosaccharide 5 of structure D.

There are subjected to stirring at ambiant temperature, for 30 mins, in the presence of a 4 Å powder molecular sieve, the solution of the compound 22 (208 mg; 0.134 mmoles) and of the halogenide 5 (350 mg; 0.67 mmoles) in dichloroethane (8 ml). After cooling to −20° C., sym-collidine (114 μl) is added and then silver triflate (201 mg; 0.74 mmoles). After one hour the reaction mixture is diluted with dichloromethane and filtered. The solution is washed (KHSO$_4$ 10%, water), dried (Na$_2$SO$_4$) and concentrated to dryness. The residue obtained (410 mg) is chromatographed on silica gel, giving the pentasaccharide 23 (203 mg; 77.5%) in foam form.

$[\alpha]_D$: +57° (c 1; chloroform).

(h) Liberation of the —OH groups blocked by acetyl groups.

Compound 23 (193 mg; 0.098 mmole) is dissolved in a mixture of chloroform (5 ml), methanol (18 ml) and water (2.5 ml). Then, drop by drop, a 5N soda solution (2.5 ml) is added. After seven hours of reaction, the reaction mixture is diluted with chloroform (50 ml), then acidified by the addition of aqueous hydrochloric acid. The product is extracted with chloroform. The chloroform phase is washed with water to neutral pH. The product is then methylated by the addition of diazomethane. The syrup obtained after evaporation to dryness is purified on a silica gel column (Lobas Merck, type A), diluted by a (chloroform→meethanol/-chloroform; 1/40; v/v) gradient. In this way, the pure compound 24 (96 mg; 55%) is obtained.

$[\alpha]_D$: +45° (c 1; chloroform).

(i) Sulfation of the liberated —OH groups.

The compound 24 (88 mg; 0.049 mmole) dissolved in anhydrous DMF (1.5 ml) is sulfated for about 14 hours at 50° C. by the complex trimethylamine/SO$_3$ (72 mg, 0.5 mmole). The mixture is then diluted by the addition of chloroform (0.75 ml) and methanol (0.75 ml), then chromatographed on a Sephadex LH-LO gel column, eluted by a chloroform/methanol (1/1; v/v) mixture. The fractions containing the derivative 25 are combined, concentrated and the product is purified on silica gel (ethyl acetate/pyridine/acetic acid/water; 160/77/19/42 v/v/v/v). In this way, the derivative 25 is obtained after a passage over a Sephadex SP25 Na$^+$ ion exchanger. This product is in the form of a white powder (97 mg; 89%).

$[\alpha]_D$: 36° (c 1; methanol).

(j) Liberation of the —OH groups blocked by benzyl groups, transformation of the —N$_3$ groups into —NH-SO$_3$ groups and of the —COOMe groups into —COO$^-$ groups The compound 25 (55 mg; 0.025 mmole) is hydrogenated in a methanol/water (9/1) mixture in the presence of a catalyst (Pd/C, 5%; 50 mg); After eight hours, hydrogenation is complete. After filtration and concentration to dryness, the product obtained is dissolved in water, the pH is brought to 9.5, then kept at this value for the whole duration of the reaction. Then, the complex pyridine/SO$_3$ is added at time 0 (54 mg), 30 minutes (27 mg) and one hour (27 mg). After one night, the reaction mixture is de-salted by means of a Sephadex G 50 gel column (1.8×40 cm) equilibrated in water. The fractions containing the product 26 are concentrated, and then the residue is deposited on a column (1.25×145 cm) of Sephadex G 25 eluted with 0.2M sodium chloride. The fractions containing the pentasaccharide 26 are passed through an anion exchanger (Biorex AG 1×2 Cl$^-$; 1.6×15 cm). The derivative 26 is then eluted by a sodium chloride gradient (0,5→3M). It is obtained pure after desalting (Sephadex G 25) and freeze-drying. It is a whitish powder (10 mg; 30%).

$[\alpha]_D$: +40° (c 1; water)

The spectral characteristics in NMR are as follows:
$^1$H-NMR: (in D$_2$O with respect to the internal TSP) unit D: 5.64 (H-1); 3.30 (H-2); 3.63 (H-3); 3.57 (H-4); 3.90 (H-5); 4-4.5 (H-6.6); Unit E: 4.62 (H-1); 3.40 (H-2); 3.87 (H-3); Unit F: 5.45 (H-1), 3.25-3;30 (H-2); Unit G: 5.24 (H-1); 4.33 (H-2); 4.20 (H-3); 4.11 (H-4); 4.81 (H-5); Unit H: 5.44 (H-1); 4.70 (H-1); 3.25 (H-2) 3.05 (H-2); 3.69 (H-3); 3.79 (H-4).

Figure 5:
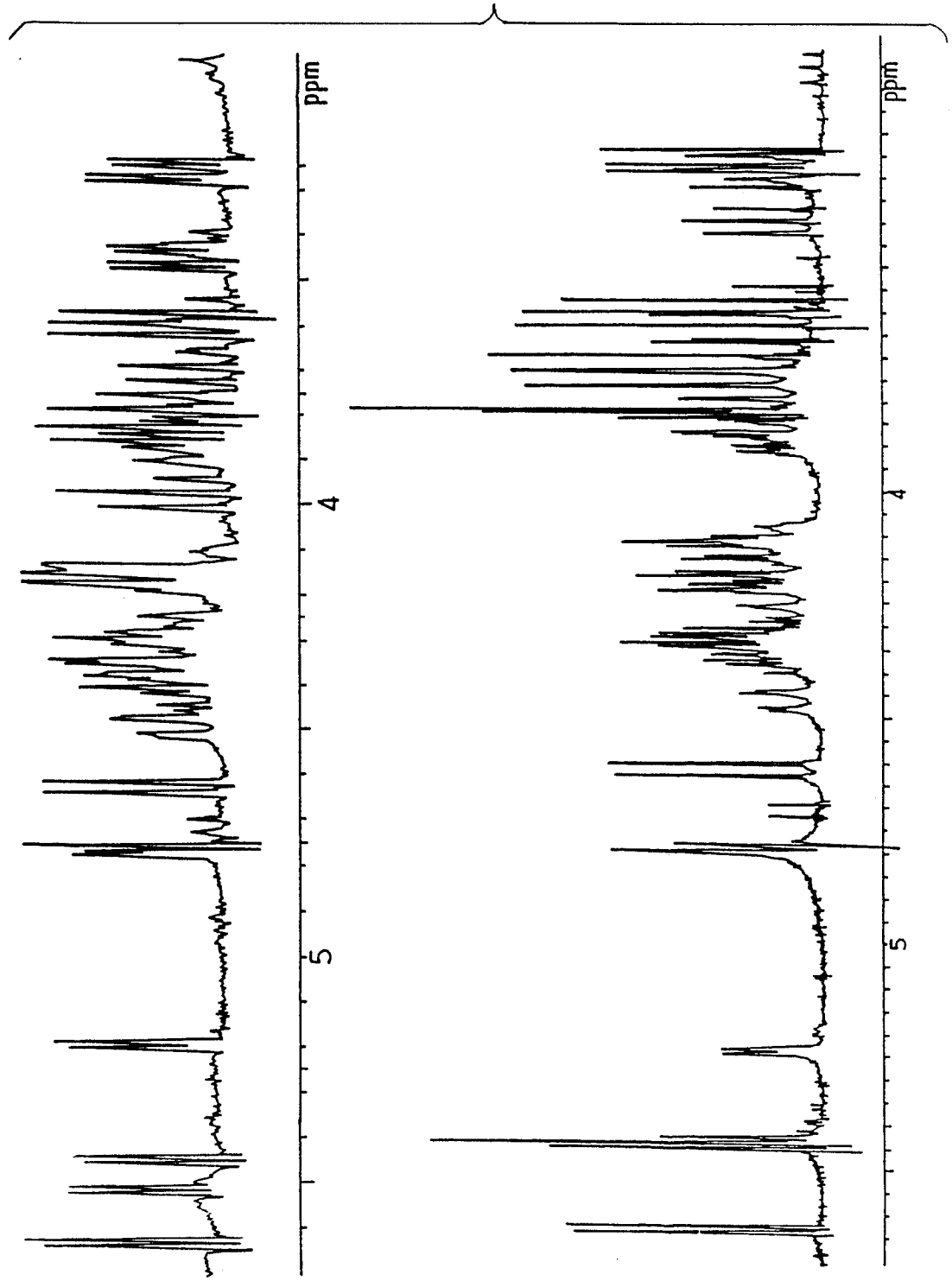

The NMR 1H spectrum of this tetrasaccharide is reported in FIG. 5, in the lower portion. By way of comparison, there is indicated in the upper portion, the NMR spectrum of the corresponding pentasaccharide including a —OSO$_3$$^-$ group at the 3 position of the F unit. The signal at 5.51 ppm observed with DEFGH including the —OSO$_3$$^-$ group on the F unit at the 3 position is attributed to the anomeric proton of the glucosamine 3-O-sulfate unit. This signal is displaced by about 5.45 ppm for the non sulfated corresponding unit F and is superposed on the corresponding signal of the unit H.

We claim:

1. A pure, synthetic tetrasaccharide having the formula

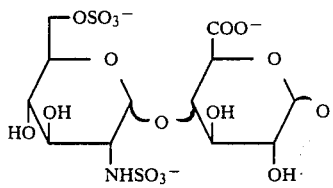

2. A pure, synthetic tetrasaccharide having the formula

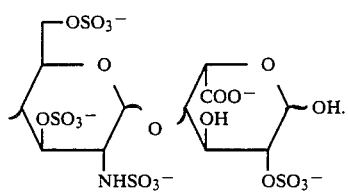

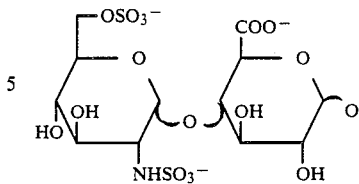

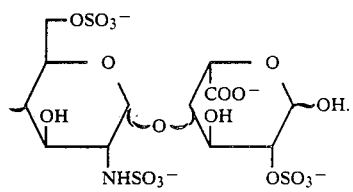

3. The pure synthetic tetrasaccharide of claim 1 wherein a salt is formed with a cation selected from the group consisting of sodium, magnesium, calcium, and triethylammonium.

4. The pure synthetic tetrasaccharide of claim 2 wherein a salt is formed with a cation selected from the group consisting of sodium, magnesium, calcium, and triethylammonium.

5. The fibrinolytic pharmaceutical composition which comprises a pharmaceutically acceptable carrier and a therapeutically effective amount of the tetrasaccharide of claim 1.

6. The fibrinolytic pharmaceutical composition which comprises a pharmaceutically acceptable carrier and a therapeutically effective amount of the tetrasaccharide of claim 2.

* * * * *

UNITED STATES PATENT AND TRADEMARK OFFICE
CERTIFICATE OF CORRECTION

PATENT NO. : 4,801,583

DATED : January 31, 1989

INVENTOR(S) : Petitou, et al.

Page 1 of 2

It is certified that error appears in the above—identified patent and that said Letters Patent is hereby corrected as shown below:

Col. 1, line 52, the octasaccharide should be:

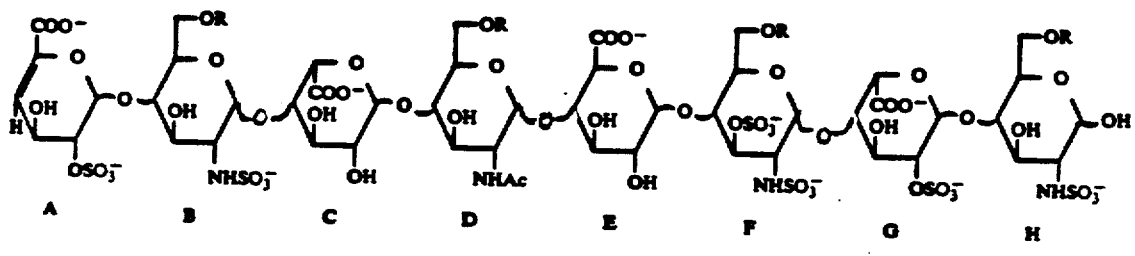

Col. 2, line 19, the pentasaccharide should be:

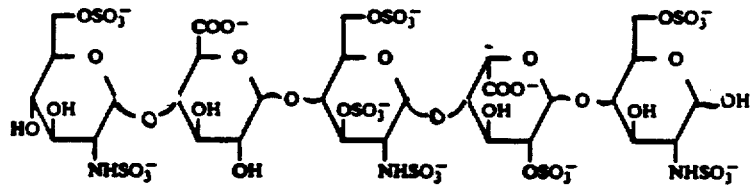

UNITED STATES PATENT AND TRADEMARK OFFICE
CERTIFICATE OF CORRECTION

PATENT NO. : 4,801,583

DATED : January 31, 1989

INVENTOR(S) : Petitou, et al.

It is certified that error appears in the above—identified patent and that said Letters Patent is hereby corrected as shown below:

Claim 1, the tetrasaccharide should be:

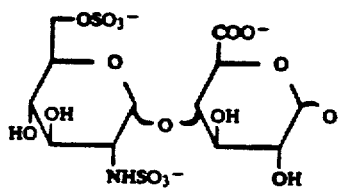

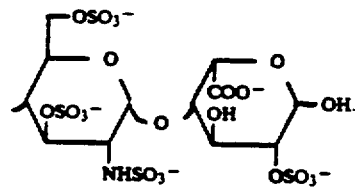

Signed and Sealed this

Thirty-first Day of July, 1990

*Attest:*

*Attesting Officer*

HARRY F. MANBECK, JR.

*Commissioner of Patents and Trademarks*